United States Patent [19]
Banik et al.

[11] Patent Number: 5,961,534
[45] Date of Patent: *Oct. 5, 1999

[54] MULTI-MOTION SIDE CUTTING BIOPSY SAMPLING DEVICE

[75] Inventors: Michael S. Banik, Cincinnati, Ohio; Donald E. Robinson, Hopkinton, Mass.

[73] Assignee: Boston Scientific Corporation, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/798,564

[22] Filed: Feb. 11, 1997

Related U.S. Application Data

[63] Continuation of application No. 08/193,255, Feb. 8, 1994, Pat. No. 5,601,585.

[51] Int. Cl.⁶ .................................................... A61B 12/32
[52] U.S. Cl. ............................................ 606/180; 128/749
[58] Field of Search .................................. 128/749, 758, 128/751, 752, 753; 606/180

[56] References Cited

U.S. PATENT DOCUMENTS

| | | |
|---|---|---|
| 612,569 | 10/1898 | Moscrop . |
| 668,647 | 2/1901 | Jaenicke . |
| 737,293 | 8/1903 | Summerfeldt . |
| 1,162,901 | 12/1915 | Cantey . |
| 1,606,497 | 11/1926 | Berger . |
| 1,867,624 | 7/1932 | Hoffman . |
| 1,891,054 | 12/1932 | Pitman . |
| 2,426,535 | 8/1947 | Turkel . |
| 2,493,979 | 1/1950 | Kudd . |
| 2,541,542 | 2/1951 | Perez et al. . |
| 2,749,909 | 6/1956 | Ullery et al. ................................. 128/2 |
| 3,001,522 | 9/1961 | Silverman . |
| 3,147,749 | 9/1964 | Marsh ......................................... 128/2 |

(List continued on next page.)

FOREIGN PATENT DOCUMENTS

| | | |
|---|---|---|
| 1215439 | 12/1970 | United Kingdom . |
| WO 93/04630 | 3/1993 | WIPO . |
| WO 94/15533 | 7/1994 | WIPO . |

OTHER PUBLICATIONS

Radical Jaw Single–Use Biopsy Forceps, Boston Scientific Corporation, 1993.
Grossman, "Gastrointestinal Endoscopy," Clinical Symposia, vol. 32, No. 3, 1980.
For the ultimate experience in multiple endoscopic biopsies, Triton.
U.S. Application No. 08/062,671 to Chu et al., filed May 17, 1993.
U.S. Application No. 08/124,272 to Diamond et al., filed Sep. 20, 1993.
U.S. Application No. 08/129,653 to Dassa et al., filed Sep. 30, 1993.

*Primary Examiner*—Michael Powell Buiz
*Assistant Examiner*—Daphja Shai
*Attorney, Agent, or Firm*—Finnegan, Henderson, Garrett, Farabow & Dunner, L.L.P.

[57] ABSTRACT

An instrument for obtaining tissue samples from a site deep within the body. The instrument has an elongated proximal portion that is constructed to follow a long, torturous path to the site and a distal end constructed to remove a tissue sample from the body, including tissue specimens, polyps or the like. The instrument is constructed to take multiple biopsy samples without being withdrawn from the body by including a storage space along the axis of the device suitable for storage of multiple, successively taken samples. The instrument includes a side-facing sampling element constructed such that it can be actuated in a first, rotational motion about the device axis to separate a tissue sample from the body and a second, axial motion for disposing the sample axially to facilitate positioning the sample in the storage space.

33 Claims, 8 Drawing Sheets

U.S. PATENT DOCUMENTS

| | | | |
|---|---|---|---|
| 3,175,554 | 3/1965 | Stewart . | |
| 3,181,533 | 5/1965 | Heath . | |
| 3,342,175 | 9/1967 | Bulloch . | |
| 3,477,423 | 11/1969 | Griffith | 128/2 |
| 3,683,892 | 8/1972 | Harris | 128/2 |
| 3,692,020 | 9/1972 | Schied | 128/2 |
| 3,732,858 | 5/1973 | Banko | 128/2 |
| 3,882,849 | 5/1975 | Jamshidi | 128/2 |
| 3,902,498 | 9/1975 | Niederer . | |
| 3,903,892 | 9/1975 | Komiya | 128/303 |
| 3,924,608 | 12/1975 | Mitsui | 128/2 B |
| 3,955,578 | 5/1976 | Chamness et al. | 128/303 |
| 3,989,033 | 11/1976 | Halpern et al. | 128/2 |
| 3,989,049 | 11/1976 | Yoon | 128/326 |
| 3,996,935 | 12/1976 | Banko et al. | 128/276 |
| 4,007,732 | 2/1977 | Kvavle et al. . | |
| 4,020,847 | 5/1977 | Clark, III | 128/305 |
| 4,168,698 | 9/1979 | Ostergard | 128/751 |
| 4,174,715 | 11/1979 | Hasson | 128/321 |
| 4,178,810 | 12/1979 | Takahashi | 74/501 |
| 4,200,111 | 4/1980 | Harris | 128/751 |
| 4,220,155 | 9/1980 | Kimberling et al. . | |
| 4,243,048 | 1/1981 | Griffin . | |
| 4,282,884 | 8/1981 | Boebel | 128/751 |
| 4,326,530 | 4/1982 | Fleury, Jr. | 128/303 |
| 4,427,014 | 1/1984 | Bel et al. | 128/751 |
| 4,461,305 | 7/1984 | Cibley | 128/754 |
| 4,493,320 | 1/1985 | Treat | 128/303 |
| 4,522,206 | 6/1985 | Whipple et al. | 128/312 |
| 4,574,803 | 3/1986 | Storz | 128/305 |
| 4,620,547 | 11/1986 | Boebel | 128/754 |
| 4,646,738 | 3/1987 | Trott . | |
| 4,651,752 | 3/1987 | Fuerst . | |
| 4,651,753 | 3/1987 | Lifton | 128/751 |
| 4,662,371 | 5/1987 | Whipple et al. | 128/312 |
| 4,682,606 | 7/1987 | DeCaprio . | |
| 4,693,257 | 9/1987 | Markham | 128/752 |
| 4,708,147 | 11/1987 | Haaga . | |
| 4,712,550 | 12/1987 | Sinnett . | |
| 4,735,215 | 4/1988 | Goto et al. | 128/754 |
| 4,763,668 | 8/1988 | Macek et al. | 128/751 |
| 4,785,826 | 11/1988 | Ward . | |
| 4,817,630 | 4/1989 | Schintgen et al. | 128/751 |
| 4,830,002 | 5/1989 | Semm | 128/321 |
| 4,867,156 | 9/1989 | Stack et al. | 128/305 |
| 4,881,550 | 11/1989 | Kothe | 128/752 |
| 4,887,612 | 12/1989 | Esser et al. | 128/751 |
| 4,903,709 | 2/1990 | Skimmer | 128/754 |
| 4,926,877 | 5/1990 | Bookwalter | 128/754 |
| 4,936,845 | 6/1990 | Stevens . | |
| 4,953,559 | 9/1990 | Salerno | 128/751 |
| 4,971,067 | 11/1990 | Bolduc et al. | 128/751 |
| 4,976,269 | 12/1990 | Mehl | 128/754 |
| 4,986,825 | 1/1991 | Bays et al. | 604/22 |
| 5,026,379 | 6/1991 | Yoon | 606/141 |
| 5,052,402 | 10/1991 | Bencini et al. | 128/751 |
| 5,074,311 | 12/1991 | Hasson | 128/754 |
| 5,085,659 | 2/1992 | Rydell . | |
| 5,098,440 | 3/1992 | Hillstead | 606/108 |
| 5,111,828 | 5/1992 | Kornberg et al. | 128/754 |
| 5,133,360 | 7/1992 | Spears . | |
| 5,133,727 | 7/1992 | Bales et al. | 606/170 |
| 5,147,378 | 9/1992 | Markham | 606/206 |
| 5,148,813 | 9/1992 | Bucalo | 128/754 |
| 5,171,255 | 12/1992 | Rydell . | |
| 5,172,700 | 12/1992 | Bencini et al. | 128/751 |
| 5,195,533 | 3/1993 | Chin et al. | 128/754 |
| 5,197,484 | 3/1993 | Kornberg et al. | 128/754 |
| 5,211,655 | 5/1993 | Hasson | 606/205 |
| 5,224,488 | 7/1993 | Neuffer | 128/751 |
| 5,238,002 | 8/1993 | Devlin et al. | 128/751 |
| 5,242,461 | 9/1993 | Kortenbach et al. . | |
| 5,251,641 | 10/1993 | Xavier | 128/754 |
| 5,267,572 | 12/1993 | Bucalo | 128/754 |
| 5,292,310 | 3/1994 | Yoon . | |
| 5,331,971 | 7/1994 | Bales et al. | 128/751 |
| 5,335,671 | 8/1994 | Clement . | |
| 5,342,390 | 8/1994 | Slater et al. | 606/205 |
| 5,373,854 | 12/1994 | Kolozsi . | |
| 5,375,608 | 12/1994 | Tiefenbrun et al. . | |
| 5,383,471 | 1/1995 | Funnell | 128/751 |
| 5,394,887 | 3/1995 | Haaga | 128/754 |
| 5,471,992 | 12/1995 | Banik et al. | 606/170 |

MULTI-MOTION SIDE CUTTING BIOPSY SAMPLING DEVICE

This is a continuation of application Ser. No. 08/193,255, filed Feb. 8, 1994. U.S. Pat. No. 5,601,585.

FIELD OF THE INVENTION

This invention relates to taking samples of tissue from the body.

BACKGROUND OF THE INVENTION

Tissue samples can be examined in a laboratory to determine the presence of a pathological disorder (e.g. malignancy). Often, the samples must be obtained from deep within the body using a medical sampling instrument that is introduced beneath the skin. It is usually best to obtain several samples around the location where the disorder is suspected so that the presence and progress of disease, if any, can be accurately determined. The samples must be catalogued according to the location from which each sample is taken and the integrity of the samples must be maintained for the subsequent laboratory analysis.

SUMMARY OF THE INVENTION

In an aspect, the invention features an instrument for obtaining tissue samples from a site deep within the body. The instrument has an elongated proximal portion that is constructed to follow a long, torturous path to the site and a distal end constructed to remove a tissue sample from the body, including tissue specimens, polyps or the like. The instrument is constructed to take multiple biopsy samples without being withdrawn from the body by including a storage space along the axis of the device suitable for storage of multiple, successively taken samples. The instrument includes a side-facing sampling element constructed such that it can be actuated in a first, rotational motion about the device axis to separate a tissue sample from the body and a second, axial motion for disposing the sample axially to facilitate positioning the sample in the storage space.

Embodiments may include one or more of the following features. The sampling element has an integral, axially adjacent sample-engaging surface for engaging a sample during axial motion of the element. The sampling element is a tube-form including a side-facing cutout defining a cutting surface and the sample engaging surface, and the storage space is defined by a portion of the tube-form adjacent the cutout. The storage space is proximal of the cutting element. The instrument includes a retention formation constructed such that the sample can be moved in a first axial direction by the sampling element into contact with the retention formation. The sampling element can be moved in the second axial direction while the sample is retained axially stationary by the retention formation. The retention formation is a high friction surface. The sampling element is constructed to prevent abrasion of the sample against the retention formation as the sample is moved axially in the first axial direction. The instrument includes an outer sleeve wherein the sampling element is moveable relative to the outer sleeve, and the retention formation is provided on the outer sleeve. The retention formation is provided on a small portion of the interior surface of the outer sleeve that is about equal to or less than the circumferential width and axial length of the side-facing cutout of the sampling element. The sampling element includes a scraping surface constructed to move between a tissue sample and a retention formation to facilitate transfer of the sample into the storage space as the sample element in the second axial direction. The retention formation is formed by sandblasting. The sleeve includes a side-facing opening through which tissue may pass to be engaged by the cutting surface of the sampling member. The interior sample contacting surfaces of the storage space include a low friction coating that allows easy axial relative displacement of the surfaces and the sample. The low friction coating is provided by a hydrogel coating. The instrument includes an axially moveable sample-retaining element constructed to engage and maintain samples in the storage space as the sampling element moves axially into a cutting position.

Other features and advantages follow.

BRIEF DESCRIPTION OF THE DRAWING

We first briefly describe the drawings.

DESCRIPTION OF THE PREFERRED EMBODIMENTS

Figure 1:
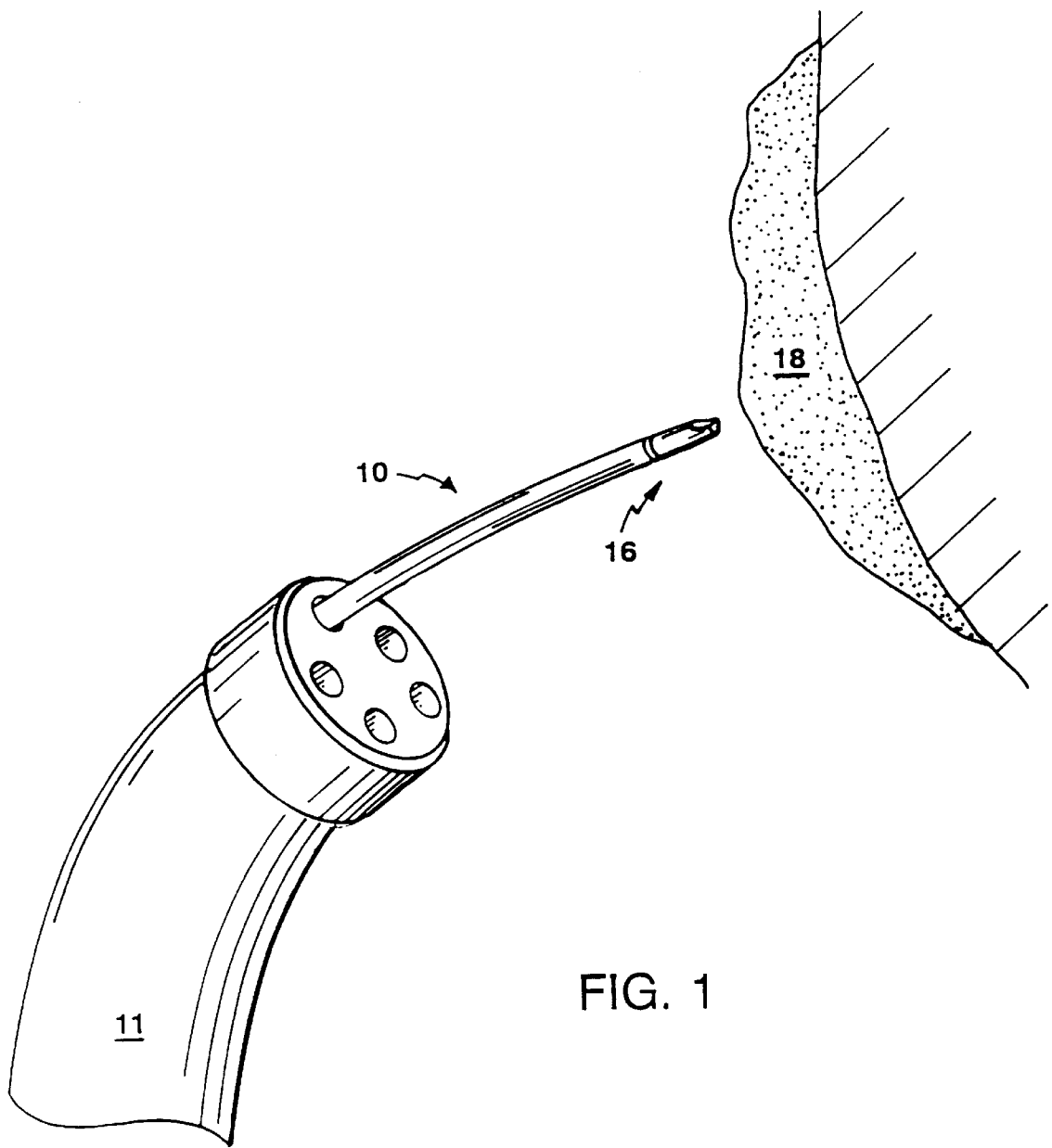
FIG. 1 is a perspective view of an embodiment of the invention being delivered into the body through an endoscope.

Referring to FIG. 1, the device 10 for multiple biopsy sampling may be delivered into the body through the channel of an endoscope device 11 (e.g., gastroscope, sigmoidoscope, or colonoscope). The endoscope device typically has a length of about 100–250 cm and a channel diameter of 2.0–3.8 mm, typically about 2.8 mm. A distal sampling portion 16 is extended from the endoscope for cutting and storing a sample of tissue from a body surface 18 of a patient (e.g. from a surface in the gastrointestinal tract or bronchial tract). The device has a diameter of preferably around 1.8–2.4 mm, typically about 2.3 mm or less and is of sufficient flexibility so it passes easily though the channel when the endoscope follows a tortuous body passageway. The endoscope includes other lumens for water, air, suction, and viewing. Devices according to the invention can be adapted to be introduced to sites (e.g., urinary tract, reproductive organs, cardiac tissue, or the like) deep within the body by other means. For example, a device can be configured with a lumen so that it can be advanced over a guidewire, e.g., in vascular applications. The device may be passed through an introducer or guiding catheter in, e.g., cardiac applications. The sampling and storage arrangements may be useful in open surgery applications.

Figure 2:
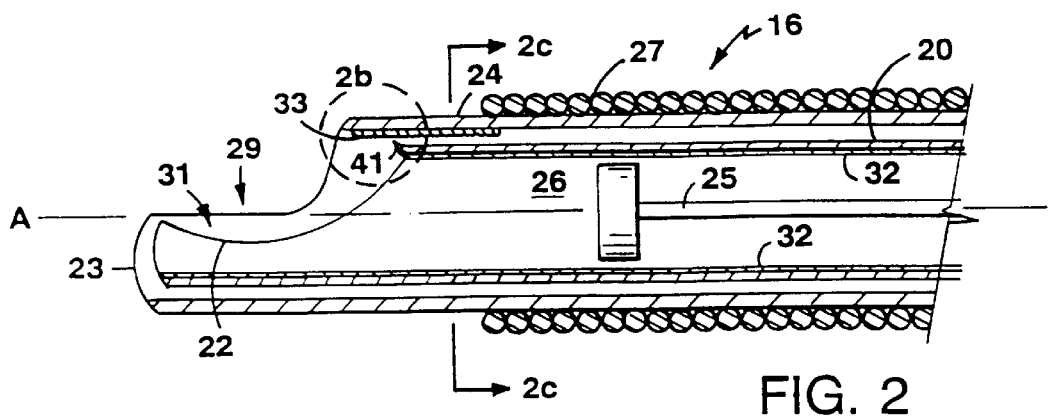
FIG. 2 is a cross-sectional view of an embodiment of the invention.
Figure 2C:
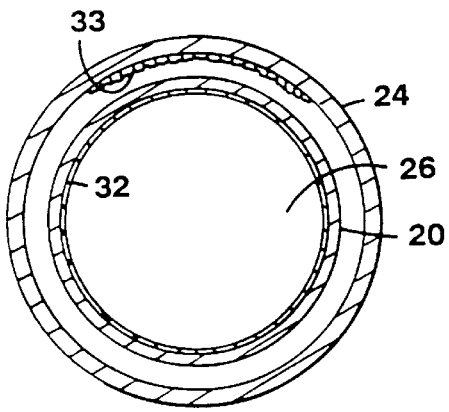
FIG. 2c is an end on cross section taken along the lines cc in FIG. 2.
Figure 2A:
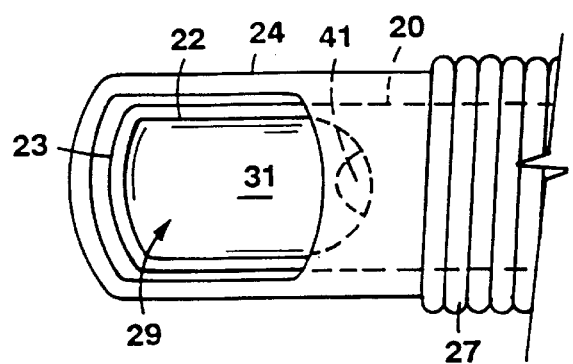
FIG. 2a is a top view of the embodiment.

Referring to FIGS. 2–2c, the sampling portion 16 includes an outer sleeve 24 concentrically positioned about an inner, generally tubular member 20. The sleeve 24 includes a side-facing opening 29 at its distal portion and a generally tubular body at its proximal portion. The inner tubular member 20 has a side-facing cutting member at its distal portion and a generally tubular proximal portion defining a sample storage space 26. The cutting member includes a side-facing opening 31 defined at its periphery by sharp cutting edges 22 and a distal end 23 that extends partially across the radius of the member 20. The member 20 is actuatable in two motions. It can be rotated about the device axis A to cut a sample from a tissue surface. It can also be moved axially to pull the cut sample into the storage space 26 where previous samples can be stored while subsequent samples are being taken, thus allowing multiple samples to be taken without removing the device from the endoscope.

Figure 2B:
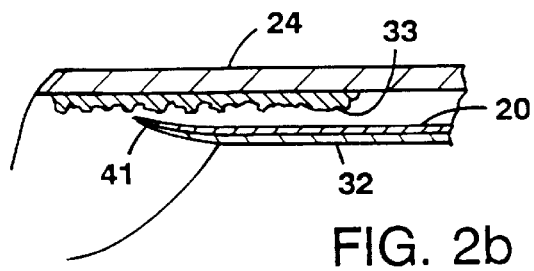
FIG. 2b is a greatly enlarged view of the area in circle b in FIG. 2.

Referring particularly to FIG. 2b, the interior walls of member 20 are provided with a low friction surface, for example, by providing a coating 32. Referring as well to FIG. 2c, the sleeve 24 includes a roughened high friction segment 33 along its inner surface at a location adjacent the opening 29. The high friction segment 33 is provided at only a small axial and circumferential portion of the interior wall of the sleeve 24 so it does not interfere with the motions of the member 20. The remaining portions of the inner wall of the member 24 may include a low friction coating to facilitate ample movement and the motions of member 20. As will be discussed further below, the high friction segment 33 on the sleeve, in cooperation with the low friction coating 32 on the interior of the member 20, permits cut samples to be urged into the sample storage space 26 as the member 20 is advanced distally to prepare it for taking further samples. Moreover, the location of the segment and the construction and rotational actuation of the member 20 prevents the sample from being abraded by the segment 33 as it is drawn axially proximally. The member 20 is also provided with a scraping element 41 that extends radially somewhat so that it lightly contacts the interior surface of the sleeve to help guide the sample into the storage space.

The device also includes an axially moveable discharge pusher 25 for removing the samples from the storage space. A flexible coil 27 is attached to the proximal portion of the sleeve 24. The coil may be provided within a slippery, flexible polymer sleeve (not shown) as known in the art. The rotational and axial motions of the member 20 can be controlled from the proximal portions of the device outside the body by a torqueable control wire (not shown) that is attached to the distal portions of the member 20 and extends proximally.

Figure 3:
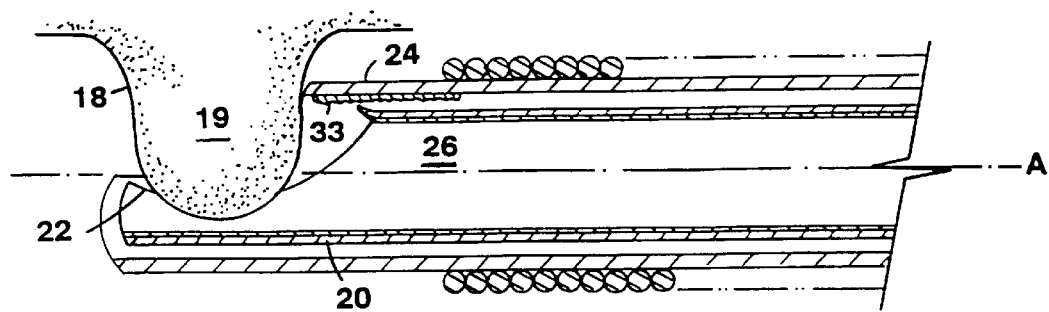
FIGS. 3–3e illustrate a use of the embodiment.
Figure 3A:
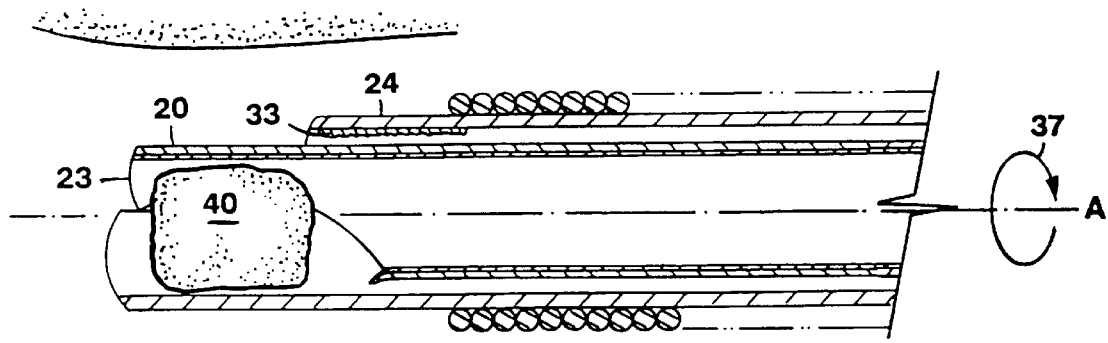
Figure 3B:
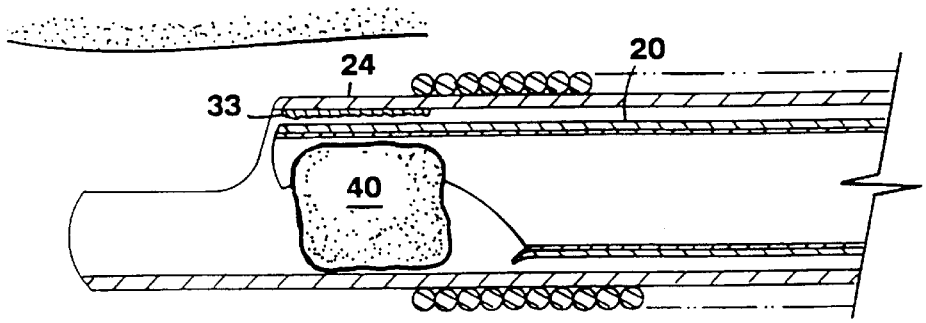
Figure 3C:
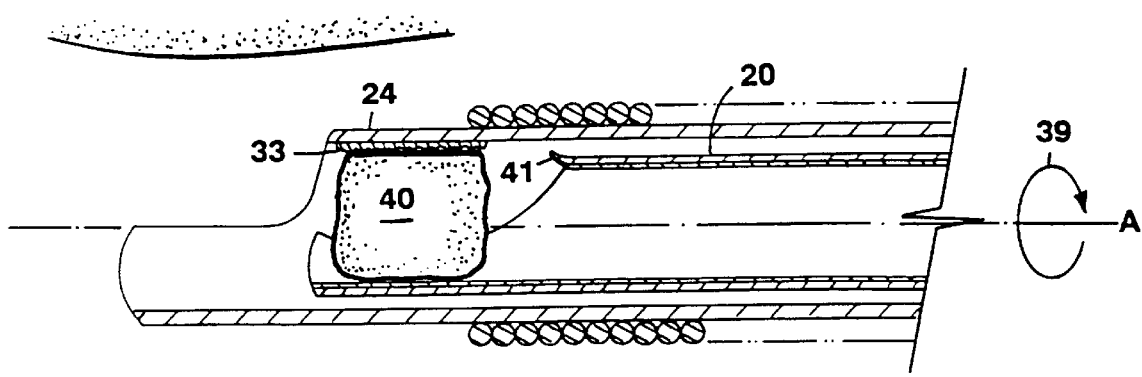
Figure 3D:
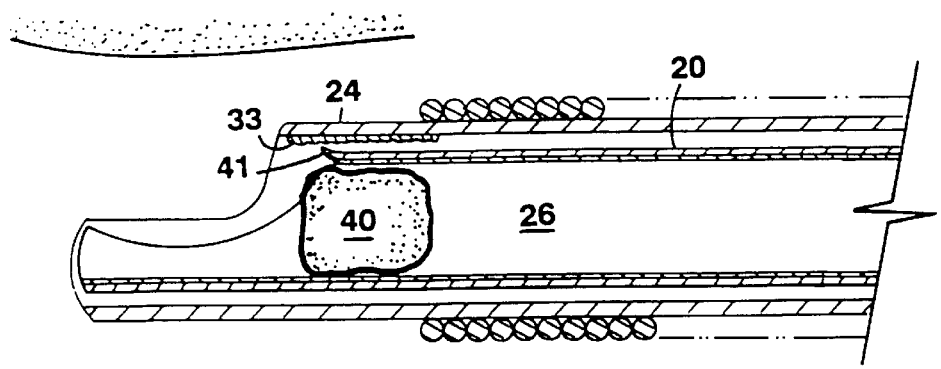
Figure 3E:
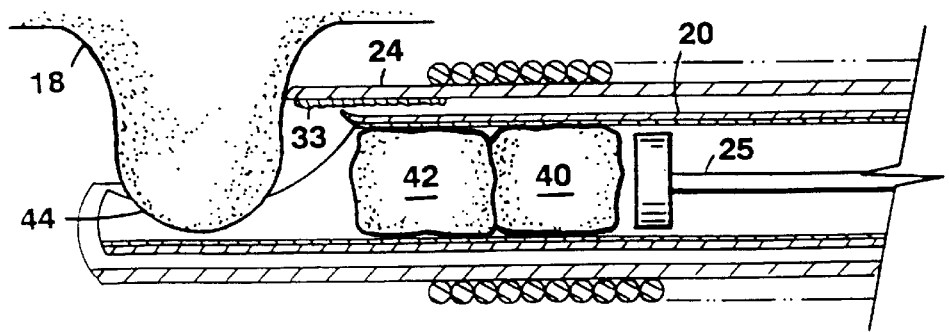

Referring to FIGS. 3–3e, particularly to FIG. 3, in use, the device is positioned adjacent a tissue area, such as a polyp feature 19 which is to be sampled. The device may be urged against the tissue surface so that the feature 19 passes through the openings 29, 31 of the sleeve 24 and the member 20.

Referring particularly to FIG. 3a, the member 20 is rotated 1800 about axis A causing a shearing action of cutting surface 22 upon the tissue surface 18 (arrow 37). The first sample, sample 40, is thus separated from the tissue surface and captured between the cutting portion of the member 20 and the interior walls of the sleeve 24.

Referring to FIG. 3b, the member 20 is then moved axially proximally, causing the radially extending end 23 of the member to engage the distal portion of the cut sample 40 and move the sample proximally. During axial motion, the sample is not rubbed against the high friction segment 33 of the sleeve. Instead, with the member 20 oriented as shown, the outer surface of the member 20 is exposed to the high friction segment and the sample 40 engages only the relatively low friction portions of the interior surface of the sleeve. This is an advantage since the sample is not abraded as it moves distally; abrading the sample could damage it and make later biopsy analysis more difficult. The sample is withdrawn proximally until it reaches an axial location that is in alignment with the high friction surface 33.

Referring to FIG. 3c, the member 20 is again rotated 180° about its axis. Because of the low friction surfaces on the inner walls of member 20, the member rotates about the sample, which remains substantially axially stationary, although it moves radially somewhat as the member 20 slips around it. By this rotation, the sample 40, extending through the opening 29, is placed in contact with the high friction segment 33 of the sleeve 24.

Referring to FIG. 3d, the member 20 is then extended distally to prepare the device for taking another sample. The sample 40 does not travel axially with the member 20 but is instead restrained from axial motion by the segment 33. Moreover, as the member moves axially, the sample slips into storage area 26 of member 20 since it slides easily on the high friction surfaces on the walls of member 20. The scraper 41, which is angled slightly so it engages the segment 33, acts like a spatula to help slip the sample into the storage area as the member 20 moves distally.

Referring to FIG. 3e, subsequent samples 42 can be taken without removing the device from the endoscope by repeating the above sequence. Samples are brought into the sample storage space 26 in the order in which they were collected. To remove the samples from the device, the push rod 25 is moved axially distally and each sample is removed through the openings 29 and 31, for example, using forceps.

The member 20 and sleeve 24 can be formed of biocompatible materials such as stainless steel, aluminum, or plastics. The length of the member and the sleeve are relatively short, e.g., on the order of about 1 inch, so the device can be passed through tortuous passageways without being hung up because of the stiffness of the end 16. The device is preferably dimensioned to take and store at least five samples before removing it from the body. The high friction segment 33 may be formed, for example, by sandblasting or etching, or it may be formed by depositing a high friction adhesive coating on the inner wall of the sleeve. The low friction surface on the interior walls of the member 20 may be provided by depositing a coating of a polymer such as teflon or, more preferably, a hydrogel. A suitable hydrogel is discussed in Fan U.S. Pat. No. 5,091,205, the contents of which is incorporated herein by reference. For embodiments constructed for use in vascular applications, the hydrogel coating can be made antithrombogenic, as discussed in Sahatjian U.S. Pat. No. 5,135,516, which is also incorporated herein by reference. A low friction coating may also be provided on the outer surfaces of the member 20 and the inner surfaces of the sleeve 24 (except for the segment 33) to reduce frictional resistance to the motions of the member 20. The low friction coating is low compared to the high friction segment 33 of the sleeve 24. In embodiments, the interior walls of the member 20 may have sufficiently low friction without a coating or further treatment. The scraper 41 may also have a high friction inner and/or outer surface. The scraper 41 preferably is a thin extension from the member 20 that has some elasticity that allows it to engage the high friction segment of the sleeve without binding as the member is moved distally. The scraper may be omitted in embodiments where there is sufficiently small clearance, e.g., on the order of 0.001 inch, between the sleeve 24 and the member 20. The proximal portion of the control wire outside the body may include index markings that indicate the axial location of the member 20 relative to the sleeve 24.

Other Embodiments

Figure 4:
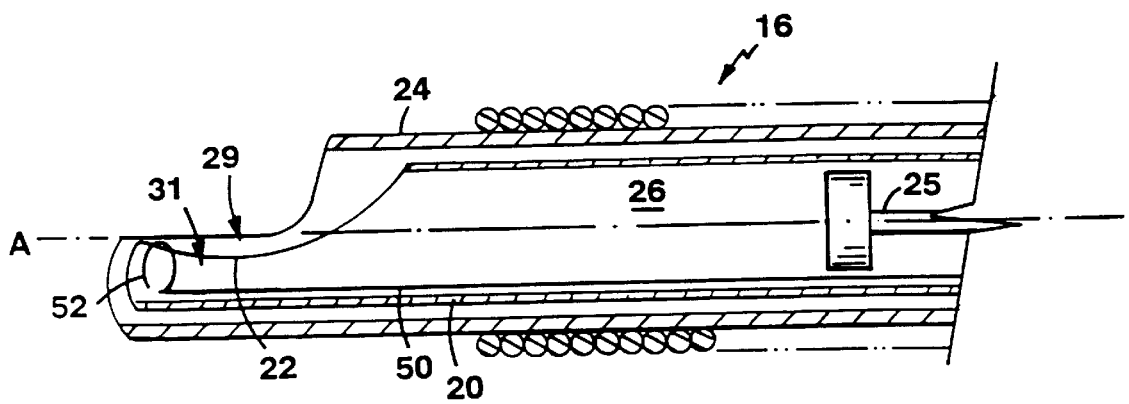
FIG. 4 is a cross-sectional view of an additional embodiment of the invention.
Figure 4A:
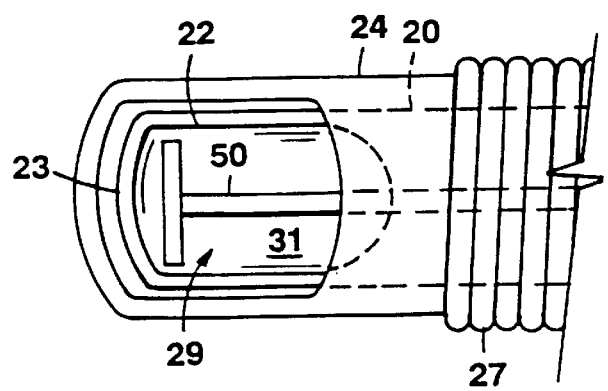
FIG. 4a is a top view of the additional embodiment.

Referring to FIGS. 4–4a and 5–5e, in another embodiment, the sampling portion 16 includes an axially moveable sample indexer 50 with a sample engaging head 52. In this embodiment, the high friction segment of the sleeve 24 may be omitted. Samples move proximally when engaged by the head but because the indexer 50 is narrow and may include a low friction coating samples do not move distally when the head is advanced (FIG. 4a).

Figure 5:
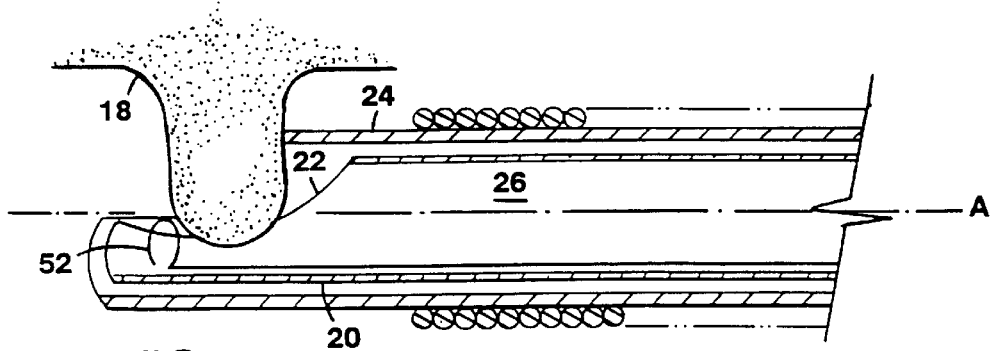
FIGS. 5–5f illustrate a use of the additional embodiment.
Figure 5A:
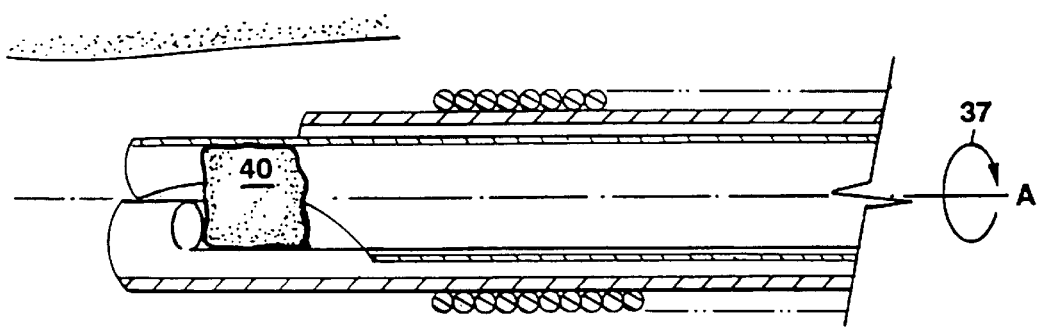
Figure 5B:
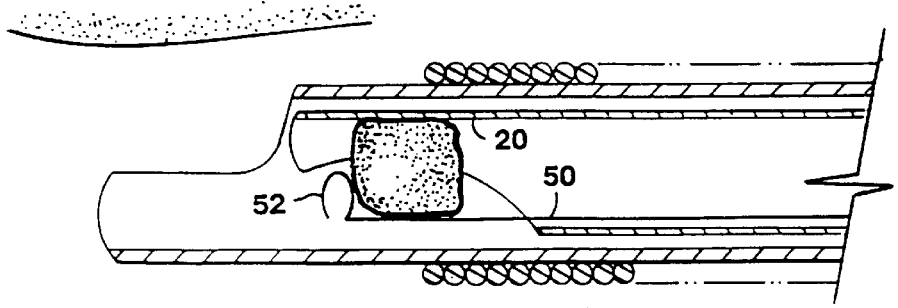
Figure 5C:
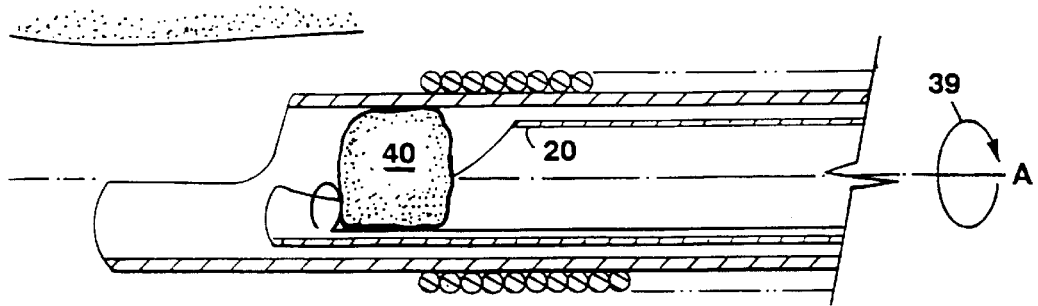
Figure 5D:
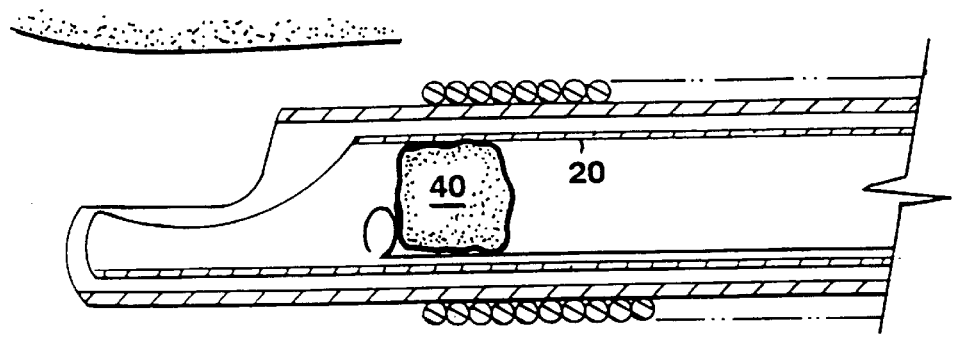
Figure 5E:
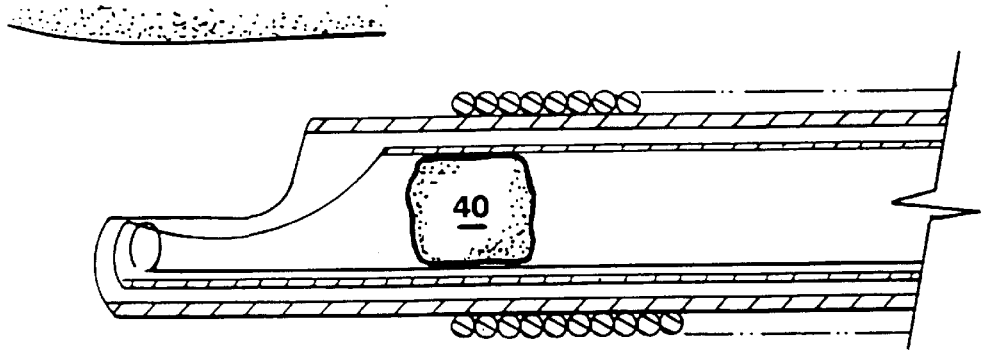
Figure 5F:
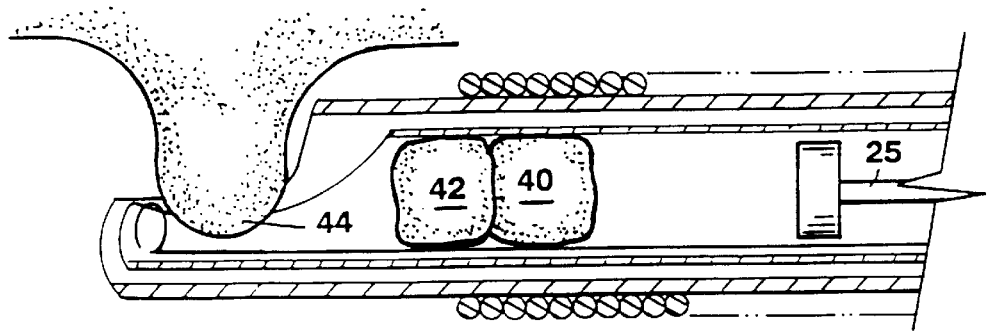

Referring to FIGS. 5–5f, particularly FIG. 5, in use, cutting surface 22 is first brought close to tissue surface 18 where a sample is to be taken. The sample indexer is extended axially such that the head 52 does not substantially obstruct the opening 29.

Referring particularly to FIG. 5a, member 20 is rotated about axis A causing a shearing action of cutting surface 22 upon tissue surface 18. The sample is separated from the tissue and first sample 40 is collected.

Referring to FIG. 5b, both member 20 and sample indexer 50 are pulled axially proximally. The head 52 and the distal end 23 of the member 20 engage the sample and pull it axially proximally. Referring to FIG. 5c, the member 20 is then again rotated about axis A.

Referring to FIG. 5d, the member 20 is then pushed axially distally to prepare to take another sample. While the member 20 is being pushed axially distally, sample indexer 50 remains in its proximal position to retain sample 40 in sample storage space 26.

Referring to FIG. 5e, the sample indexer is then advanced axially distally to its original position. Subsequent samples can then be taken.

Referring to FIG. 5f, subsequent samples 42 and 44 can be taken without removing the device from the endoscope by repeating the above sequence. The samples are brought into the sample storage space in the order in which they were collected. To remove samples from the device, push rod 25 is moved axially distally and each sample is removed through access hole 28, for example, using forceps.

Figure 6:
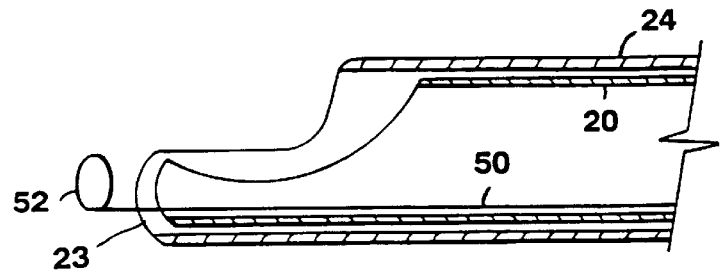
FIG. 6 is a cross-sectional view of an additional embodiment.
Figure 6A:
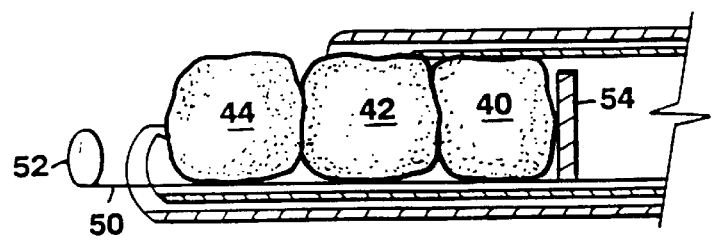
FIG. 6a is a cross-sectional view of an additional embodiment.

Referring to FIG. 6, in other embodiments, member 20 and sleeve 24 are modified by placing a hole through their distal ends so that sample indexer 50 can thus be advanced to push the head 52 distally through the end 23 of the member 20 and sleeve 24 allowing more room for sample capturing and for sample access during sample removal. Referring to FIG. 6a, in embodiments, sample indexer 50 also carries a sample discharge surface 54 that can be used to remove samples from the storage space by extending the indexer distally.

Figure 7:
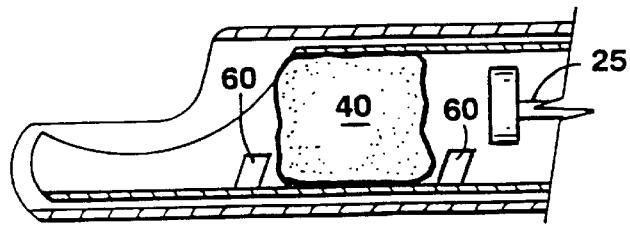
FIG. 7 is a cross-sectional view of another embodiment.

Referring to FIG. 7, in embodiments, member 20 has index points 60 in the storage space. The index points 60 are flexible radial extensions from the inner wall of the member 20 that are angled to be easily bent when samples are urged proximally but inhibit the samples from moving distally. The index points 60 can be bent (elastically in a multi-use device) distally to remove the samples from the storage space when greater force is applied by the discharge pusher 25.

Figure 8:
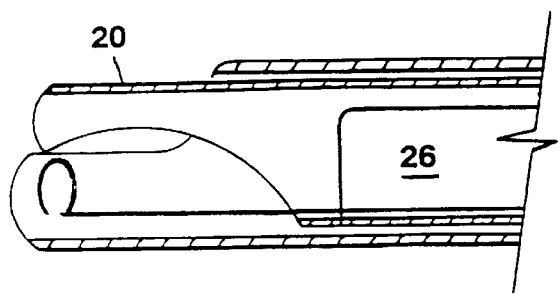
FIG. 8 is a cross-sectional view of another embodiment.

Referring to FIG. 8, in still further embodiments, proximal portions of member 20 are removed to reduce the frictional contact with the inner surface of the sleeve 24. The sample space 26 is defined by the remaining arc-form of the member 20 and the proximal portions of the sleeve 24.

A system for taking multiple biopsy samples is taught in Chu "Instruments for Collecting Multiple Biopsy Specimens", U.S. Ser. No. 062,671, filed May 17, 1993, the entire contents of which is hereby incorporated by reference. Another system is taught in U.S. Ser. No. 08/124,272, filed Sep. 20, 1993, which is also incorporated herein by reference. Another system is taught in U.S. Ser. No. 08/129,653, filed Sep. 30, 1993 which is also incorporated herein by reference. Another system is taught in U.S. Ser. No. 08/146, 447, filed Oct. 29, 1993, which is hereby incorporated by reference. Another system is taught in an application entitled "Moveable Sample Tube Multiple Biopsy Sampling Device", by Banik et al., filed the same day as this application, which is hereby incorporated by reference. Another system is taught in an application entitled "Multi-Motion Cutter Multiple Biopsy Sampling Device", by Banik and Robinson, filed on the same day as this application, which is also incorporated herein by reference.

Still other embodiments are within the following claims. For example, a barbed spear-form can also be used to hold samples in the storage area.

Other embodiments follow.

What is claimed is:

1. An instrument for obtaining multiple tissue samples from tissue sites within a body while the instrument remains in the body, the instrument comprising:

an elongated proximal portion for following a path to said tissue sites; and a distal end coupled to the proximal portion for removing multiple tissue samples from the body, the distal end defining a storage space along an axis of the distal end for storage of multiple tissue samples, the distal end including a sampling element having a cutting edge defining an opening along a side of the sampling element, the sampling element being rotatable about the axis so that the cutting edge separates a tissue sample located within the opening from the body and axially movable for disposing a separated tissue sample in said storage space for storage with additional tissue samples, the distal end further including a retention formation proximate the storage space, the retention formation being axially displaceable relative to the sampling element to permit movement of a separated tissue sample in a proximal direction by said sampling element into contact with said retention formation and contacting and retaining a separated tissue sample in a stationary axial position as said sampling element moves in a distal direction.

2. The instrument of claim 1 wherein said sampling element has an integral sample-engaging surface for engaging a sample during said axial motion of said element.

3. The instrument of claim 2 wherein said sampling element is a tube, wherein said storage space is defined by a portion of said tube adjacent said opening.

4. The instrument of claim 3 wherein said storage space is proximal of said opening.

5. The instrument of claim 1 wherein said retention formation is a high friction surface.

6. The instrument of claim 5 wherein said sampling element prevents abrasion of a separated tissue sample against said retention formation as said separated tissue sample is moved in the proximal direction.

7. The instrument of claim 6 including an outer sleeve disposed over the sampling element, wherein said sampling element is axially and rotatably moveable relative to said outer sleeve, and said retention formation is provided on said outer sleeve.

8. The instrument of claim 7 wherein said retention formation is provided on a small portion of an interior surface of said outer sleeve.

9. The instrument of claim 8 wherein said sampling element includes a scraping surface extending towards the retention formation for positioning between the tissue sample and said retention formation to facilitate transfer of said tissue sample into said storage space as said sampling element moves in said.

10. The instrument of claim 8 wherein said outer sleeve includes an opening along a side of the outer sleeve through which tissue may pass to be engaged by said cutting edge of said sampling element.

11. The instrument of claim 1 wherein said retention formation is a sandblasted surface.

12. The instrument of claim 1 wherein the distal end includes interior sample contacting surfaces defining said storage space, wherein said sample contacting surfaces include a low friction coating that allows easy axial relative displacement of the sample contacting surfaces and said tissue sample.

13. The instrument of claim 12 wherein said low friction coating is a hydrogel.

14. The instrument of claim 1 further including an axially moveable sample-retaining element disposed within the sampling element to engage and maintain tissue samples in said storage space as said sampling element moves axially into a cutting position.

15. An instrument for obtaining multiple tissue samples from a body, the instrument comprising:
an outer member defining a first opening along a side of the outer member;
an inner member disposed within the outer member, the inner member defining a storage space therein for storage of multiple tissue samples, the inner member including a cutting edge defining a second opening along a side of the inner member, the inner member being rotatably disposed relative to the outer member so that the cutting edge severs a tissue sample extending within the first and second openings, the inner member being axially displaceable relative to the outer member so that axial displacement of the inner member in a proximal direction moves a severed tissue sample into the storage space for storage with additional tissue samples; and
a retention member proximate the storage space and axially displaceable relative to the inner member for contacting and retaining a severed tissue sample in a stationary axial position in the storage space upon axial displacement of the inner member in a distal direction relative to the outer member and the retention member.

16. The instrument of claim 15, wherein the outer member includes the retention member.

17. The instrument of claim 15, wherein the retention member is a high friction surface proximate the storage space.

18. The instrument of claim 15, wherein the retention member is provided on a portion of an inner surface of the outer member.

19. The instrument of claim 15, wherein the inner member is a tube and the outer member is a tube.

20. The instrument of claim 15, wherein the inner member includes a scraping element extending towards the retention member for separating a severed tissue sample from the retention member.

21. The instrument of claim 15, wherein the retention member is an indexer disposed within the inner member and axially displaceable relative to the inner member.

22. The instrument of claim 15, wherein the retention member is axially displaceable relative to the inner member and the outer member, the retention member including a head portion at a distal end of the retention member to retain a severed tissue sample in the storage space upon axial displacement of the inner member in a distal direction relative to the outer member and the retention member.

23. A method of severing and storing multiple tissue samples comprising:
providing a surgical instrument having an outer member, an inner member, and a retention member, the outer member defining a first opening along a side of the outer member, the inner member being disposed within the outer member, defining a storage space in the inner member for storage of multiple tissue samples, and including a cutting edge defining a second opening along a side of the inner member, the retention member being proximate the storage space and axially displaceable relative to the inner member;
positioning a tissue sample within the first opening and the second opening;
rotating the inner member relative to the outer member so that the cutting edge severs the tissue sample;
axially displacing the inner member relative to the outer member in the proximal direction to move the severed tissue sample into the storage space;
contacting the severed tissue sample with the retention member to retain the severed tissue sample in the storage space as the inner member is axially displaced relative to the outer member in the distal direction to align the first and second openings; and repeating the positioning, rotating, axially displacing, and contacting steps to sever and store additional tissue samples.

24. The method of claim 23, wherein the outer member includes the retention member.

25. The method of claim 23, wherein the retention member is a high friction surface.

26. The method of claim 23, wherein the retention member is provided on a portion of an inner surface of the outer member.

27. The method of claim 23, wherein the inner member is a tube and the outer member is a tube.

28. The method of claim 23, further comprising the step of separating a severed tissue sample from the retention member by a scraping element extending from the inner member towards the retention member.

29. The method of claim 28, wherein the separating step occurs as the inner member is axially displaced relative to the outer member in the distal direction to align the first and second openings.

30. The method of claim 23, wherein the retention member is an indexer disposed within the inner member and axially displaceable relative to the inner member.

31. The method of claim 23, wherein the retention member is axially displaceable relative to the inner member and the outer member, the retention member including a head portion at a distal end of the retention member.

32. The method of claim 31, wherein the contacting step includes contacting the severed tissue sample with the head portion as the inner member is axially displaced relative to the outer member in the distal direction to align the first and second openings.

33. The method of claim 32, further comprising axially displacing the retention member in the distal direction relative to the inner member and the outer member after the first and second openings are aligned.

\* \* \* \* \*

UNITED STATES PATENT AND TRADEMARK OFFICE
CERTIFICATE OF CORRECTION

PATENT NO. : 5,961,534 Page 1 of 1
APPLICATION NO. : 08/798564
DATED : October 5, 1999
INVENTOR(S) : Michael S. Banik et al.

It is certified that error appears in the above-identified patent and that said Letters Patent is hereby corrected as shown below:

In Claim 9, Col. 7, line 9, after "said" insert --distal direction--

Signed and Sealed this

Eighth Day of August, 2006

JON W. DUDAS
*Director of the United States Patent and Trademark Office*